United States Patent [19]

Nichols

[11] Patent Number: 4,804,541

[45] Date of Patent: Feb. 14, 1989

[54] TRANSDERMAL ADMINISTRATION USING BENZYL ALCOHOL

[75] Inventor: Larry D. Nichols, Arlington, Mass.

[73] Assignee: Moleculon, Inc., Cambridge, Mass.

[21] Appl. No.: 84,390

[22] Filed: Aug. 11, 1987

[51] Int. Cl.[4] .................. A61L 15/03; A61F 13/00; A61K 9/70

[52] U.S. Cl. .................. 424/449; 514/509; 514/946; 514/947; 514/169; 514/171

[58] Field of Search .............. 514/509, 946, 947; 424/449

[56] References Cited

U.S. PATENT DOCUMENTS

| | | | |
|---|---|---|---|
| 3,867,528 | 2/1975 | Ritter et al. | 514/174 |
| 4,017,615 | 4/1977 | Shastri et al. | 514/176 |
| 4,112,115 | 9/1978 | Coghlan | 514/509 |
| 4,272,516 | 6/1981 | Caldini et al. | 424/70 |
| 4,273,771 | 6/1981 | Coussediere | 514/177 |
| 4,440,778 | 4/1984 | Matsui et al. | 514/420 |
| 4,450,175 | 5/1984 | Warshaw | 514/509 |
| 4,563,346 | 1/1986 | Deckner | 514/714 |

FOREIGN PATENT DOCUMENTS

| | | | |
|---|---|---|---|
| 153200 | 8/1985 | European Pat. Off. | |
| 0183527 | 6/1986 | European Pat. Off. | 514/946 |
| 2050827A | 1/1981 | United Kingdom | 514/509 |

OTHER PUBLICATIONS

Wollman CA. 67#99866T(1967).
Menczel CA. 76#95309p (1972).
Martini CA. 102#225931d (1985).
Barry CA. 102#137721e (1985).
Bellantone CA. 105#29917B(1986).
Chem. Abstr., vol. 103, 183594j (1985).

*Primary Examiner*—Shep K. Rose

[57] ABSTRACT

A method, composition, and article for use in transdermal or percutaneous administration to humans of systemically active medicaments in the form of a solution in benzyl alcohol.

16 Claims, No Drawings

TRANSDERMAL ADMINISTRATION USING BENZYL ALCOHOL

This invention relates to a method, composition, and article for use in transdermal or percutaneous administration to humans of a systemically active medicament and pertains more specifically to a method, composition, and article for application to human skin for systemic administration of the medicament from a solution in benzyl alcohol.

It has long been known that various medicaments can be transported through the skin of a human to provide systemic and prolonged administration of the medicament. However, transdermal delivery is rendered difficult by the effectiveness of the skin's superficial barrier layer, the stratum corneum, whose structure of overlapping keratinized cells separated by thin lipid layers strongly hinders diffusion of medicaments through the skin. In general, the maximum area of skin contact which is practical for a single application of a medicament is no more than about 20 square inches or 130 square centimeters, preferably it is less than 6 square inches or 40 square centimeters, although in some cases two or more applications can be employed simultaneously on separate skin areas. Since it is well known that the therapeutically effective systemic dose of a medicament varies depending upon the identity of the medicament and the weight of the patient, the minimum flux or transport rate required for therapeutic effectiveness can readily be determined by simple arithmetic for an applicator of given area. In the case of most medicaments, the transport rate through unmodified stratum corneum is so low as to make transdermal delivery impractical. This has necessitated the use of certain liquids, often referred to as penetration aids, to enhance and facilitate diffusion of the medicament through the skin. Among such penetration aids are various amides and certain fatty acids, alone or admixed with solvents or vehicles such as dimethyl sulfoxide, polyethylene glycol, or aqueous ethanol. Unfortunately, many such penetration aids and/or solvents may be irritating to the skin or even toxic. Indeed, the best known penetration aid, dimethyl sulfoxide, is currently considered a health hazard in the United States, and ethanol/water 70/30 tends to cause skin irritation.

It has also been reported in Caldini et al. U.S. Pat. No. 4,272,516 that benzyl alcohol, employed in an amount of 5.0 to 33.33% by weight of a cosmetic composition is effective to improve absorption into the skin of various substances of a lipoid nature to change the charateristics of the skin or hair. Cutaneous absorption, the subject of the Caldini patent, has as its objective the treatment of the skin and its appendages, such as hair. This requires the accumulation of an effective local concentration of active agent within the skin itself as a not necessarily rapid consequence of the treatment. Percutaneous absorption, the subject of my invention, has as its objective the systemic treatment of nondermal conditions in the patient. This requires the rapid and sustained passage of an applied drug into and through the skin so as to enter the bloodstream at a rate sufficient to maintain therapeutic action for the intended duration of a single percutaneous application and treatment. For cutaneous treatment it is usually not critical how fast the agent enters the skin, so long as it enters more rapidly than it leaves. For percutaneous treatment it is important that both entry into and exit from the skin occur at useful rates. The contrasts between these two applications suggest that a vehicle which promotes cutaneous absorption should be poorly qualified for percutaneous delivery, and vice versa. The evidence that benzyl alcohol performs well in both applications is therefore surprising.

It has now been found that compositions containing at least 50% by weight of benzyl alcohol containing dissolved in the alcohol at least 1% by weight, based on the alcohol, of a medicament are useful in achieving high rates of transport of the medicament through the skin for systemic administration. The present invention is particularly effective in providing transdermal or percutaneous administration to humans of isosorbide dinitrate (ISDN), an antianginal drug, and of estradiol, a steroid used in treatment of post-menopausal symptoms in women. Therapeutically effective systemic doses of both drugs can be produced by applying the compositions of the present invention to as little as 20 square centimeters of skin.

Benzyl alcohol is non-irritating to the skin, non-toxic, and free from undesirable physiological effects. It is metabolized cleanly in the body to benzoic acid and excreted as hippuric acid and has been employed as a major component of certain drug solutions administered by percutaneous injection to young infants. While both ISDN and estradiol exhibit low solubility in both lipids and in water, both medicaments display substantial solubility in benzyl alcohol.

For effective systemic administration of the medicament, the dilution or solution in benzyl alcohol must be maintained in contact with the skin for a prolonged period of time. This can be accomplished for example by thickening the solution to the point where it does not readily flow and approaches a solid in properties. Appropriate thickeners or gelling agents can be added to the solution for this purpose. The substantially non-flowing solution can simply be applied to or coated on the skin; preferably, some mechanical protection in the form of a cover or bandage is provided to prevent it from being wiped off. Another method for maintaining contact between the solution and the skin is to compound the solution with a suitable inert adhesive to produce a semi-solid adhesive layer combining in one component the required payload of medicament, the benzyl alcohol solvent, and dermal adhesive. Such an adhesive layer can usefully be backed with a non-permeable covering such as foil, or plastic film to confine the medicament solution and avoid adhesion to other surfaces. The benzyl alcohol solution can also be maintained in place by imbibing or absorbing it in a suitable solid carrier such as an absorbent pad of fibrous material or a porous benzyl-alcohol-insoluble polymeric matrix, the latter being preferred. It is particularly advantageous to incorporate the medicament solution in a gelled cellulose triacetate matrix, as described for example in Nichols U.S. Pat. No. 3,846,404 incorporaed herein by reference. In general, suitable carriers are porous preferably microporous, benzyl-alcohol-insoluble materials throughout which the benzyl alcohol soluton of medicament can be distributed or dispersed so that a supply of the solution is maintained in contact with the skin. In one embodiment, the carrier is provided with means for maintaining in contact with the skin such as a layer of adhesive. The adhesive may extend only along part or all of the periphery of the face of the carrier or it may if it is sufficiently permeable, to cover the skin-contacting face of the carrier. In the simplest case, a separate strip of adhesive tape may be employed to maintain the carrier in place. Among suitable carriers are absorbent paper, fibrous batts such as cotton batting and various porous or microporous polymeric gel compositions such as partially cross-linked polyvinyl alcohol, polyvinyl pyrrolidone or polyacrylamide; and porous or microporous gels of cellulose esters or ethers including cellulose acetate, cellulose butyrate, cellulose nitrate and the like. Particularly preferred is microporous cellulose triacetate gel as pointed out above.

Overall rate of transport of the medicaments through the skin, hence the systemic concentration level of the medicament, can be adjusted by varying the area of the skin with which the solution is in contact or by varying the concentration of the medicament in the benzyl alcohol. In general it is preferred that the amount of medicament present in the benzyl alcohol be equal to at least 80% by weight of the amount present in a saturated solution in benzyl alcohol at room temperature. In any event, the amount of medicament present must be at leaast 1% by weight of the benzyl alcohol.

The rate of transport or flux of the medicament through the skin can readily be determined in vitro by placing the benzyl alcohol solution of the medicament, with the medicament suitably labelled, for example, with tritium to a final specific activity of 300 disintegrations per minute per microgram, in contact with a specimen of human epidermis, e.g. human breast epidermis, with intact stratum corneum, mounted in a conventional diffusion cell providing an exposed skin surface area of 0.34 square centimeters each. The receptor chamber of each cell is swept with a stream of 0.1M phosphate buffered (pH 7.4) isotonic saline in direct contact with the rear surface of the epidermal sample, the flow rate being maintained at approximately 2 ml per hour. Samples of the saline receptor solution are collected at two-hour intervals and assayed by a liquid scintillation counter, applying the appropriate quench correction procedure.

The following examples are intended to illustrate more fully the nature of the invention without acting as a limitation upon its scope.

EXAMPLE 1

A 10% solution by weight of radiolabelled isosorbide dinitrate in benzyl alcohol was prepared as described above and a 50 microliter sample was placed in a diffusion cell providing 0.34 square centimeter of exposed human skin in order to measure the rate of transport or flux by the procedure described above extending over a 24 hour period. The skin sample used consisted of epidermis stripped from surgically removed human skin from healthy mammaplasty subjects. The average of 3 such determinations showed essentially linear transport of ISDN at a flux rate of 0.3 mg/centimeter square/day.

A test carried out of a 17% solution of labelled ISDN in polyethylene glycol (PEG-400) under the same conditions except that the test extended for 40 hours showed a flux rate of 0.1 mg/cm$^2$/day.

EXAMPLE 2

In vivo tests of isosorbide dinitrate at a concentration of 10.5% by weight in benzyl alcohol were conducted on 5 human volunteers using in each case a 20 centimeter square sample of porous cellulose triacetate film (0.20 inch thick) prepared as described in U.S. Pat. No. 3,846,404. There were absorbed into each specimen of porous film sufficient solution to contain 122 mg of the drug. In each case the film specimen containing the benzyl alcohol solution was held securely in place under a thin polyethylene backing against the inside of the upper arm of the subject for 48 hours. During the trial there was no evidence or complaint of skin irritation; three of the subjects experienced headaches, a common side effect of ISDN therapy. Blood samples taken over the first 24 hours of the test showed an average ISDN content of 4.33 ng/ml, an effective therapeutic value. Based on a clearance of 4 L/min, the total area under the curve of blood level versus time corresponded to an average in vivo flux rate of 1.1 mg/cm$^2$/day.

Similar in vivo tests of 17.0% ISDN in PEG-400 were conducted on four volunteers using 10 cm$^2$ samples of cellulose triacetate film containing sufficient solution to contain 116 mg of drug. The medicament containing films were heat-sealed to polyethylene laminated aluminum films which were then placed in the center of 5.5 cm×5.5 cm pieces of inert sponge foam material with adhesive (3M Microfoam). Such a patch was placed on the upper left quadrant of the torso of each volunteer in a manner to achieve occlusive dermal contact. After 24 hours the patches were removed. During the trial there was no decrease in blood pressure beyond normal fluctuations. Headaches, a common ISDN side effect, were not noted. Blood samples taken over the first 24 hours of the test showed an average ISDN content of less than 0.4 ng/ml. Based on a clearance of 4 L/min, the total area under the curve of blood level versus time corresponded to an average in vivo flux of 0.3 mg/cm$^2$/day.

EXAMPLE 3

In vivo transport rate of estradiol in benzyl alcohol was measured as described above using small diffusion cells each containing 40 microliters of a 4% solution of radiolabeled estradiol in benzyl alcohol in contact with 0.34 cm$^2$ of human skin. The skin samples used consisted of epidermis stripped from surgically removed human skin from healthy mammaplasty subjects, and the measurements extended from 48 to 66 hours. The average of 14 such cells showed delivery of estradiol at an average flux of 6.24 mcg/cm$^2$/day.

What is claimed is:

1. A composition adapted to be maintained in contact with skin of a human to provide systemic administration of a medicament which consists essentially of at least 50% by weight of benzyl alcohol containing dissolved therein at least 1% by weight, based on said alcohol, of said medicament.

2. A composition as claimed in claim 1 in which said medicament is isosorbide dinitrate.

3. A composition as claimed in claim 1 in which said medicament is estradiol.

4. A composition adapted to be maintained in contact with the skin of a human so as to provide rapid and sustained penetration of a therapeutic amount of a medicament into the bloodstream which consists essentially of at least 50% by weight of benzyl alcohol containing dissolved therein at least 1% by weight of said medicament.

5. An article adapted to be maintained in contact with skin of a human to provide systemic administration of medicament to said human which comprises a solid benzyl-alcohol-insoluble porous carrier and absorbed in said carrier a composition which comprises at least 50% by weight of benzyl alcohol containing dissolved therein at least 1% by weight, based on said alcohol, of said medicament.

6. An article as claimed in claim 5 in which said medicament is isosorbide dinitrate.

7. An article as claimed in claim 5 in which said medicament is estradiol.

8. An article adapted to be maintained in contact with the skin of a human to provide rapid and sustained penetration of a therapeutic amount of a medicament into the bloodstream which comprises a solid benzyl-alcohol-insoluble porous carrier and impregnated into said carrier a composition which comprises at least 50% by weight of benzyl alcohol containing dissolved therein at least 1% by weight of said medicament.

9. Method of administering a medicament systemically to a human which comprises
   providing a composition as claimed in claim 1, and
   maintaining said composition in contact with the skin of a human.

10. Method as claimed in claim 9 in which said medicament is isosorbide dinitrate.

11. Method as claimed in claim 9 in which said medicament is estradiol.

12. Method of administering a medicament systemically to a human which comprises
    providing an article as claimed in claim 8, and
    maintaining said article in contact with the skin of a human.

13. A composition adapted to be maintained in contact with skin of a human to provide systemic administration of an effective anti-anginal amount of a medicament effective systemically for percutaneous anti-anginal therapy which consists essentially of not less than at least 50% by weight of benzyl alcohol containing dissolved therein at least 1% by weight, based on said alcohol, of said medicament.

14. A composition as claimed in claim 13 in which said medicament is isosorbide dinitrate.

15. Method of administering a medicament effective systemically for percutaneous anti-anginal therapy to a human which comprises
    providing a composition as claimed in claim 13, and
    maintaining said composition in contact with the skin of a human.

16. Method as claimed in claim 15 in which said medicament is isosorbide dinitrate.

* * * * *